United States Patent [19]
Schmoegner

[11] Patent Number: 5,122,344
[45] Date of Patent: Jun. 16, 1992

[54] CHEMICAL STERILIZER SYSTEM

[75] Inventor: John C. Schmoegner, Redondo Beach, Calif.

[73] Assignee: MDT Corporation, Torrance, Calif.

[21] Appl. No.: 472,817

[22] Filed: Jan. 31, 1990

[51] Int. Cl.$^5$ ............................................. A61L 2/24
[52] U.S. Cl. ................................. 422/111; 422/28; 422/32; 422/298; 422/305; 422/307
[58] Field of Search ................. 422/28, 32, 33–37, 422/292, 298, 299, 305, 307, 111

[56] References Cited

U.S. PATENT DOCUMENTS

| | | |
|---|---|---|
| 3,086,263 | 7/1960 | Huber . |
| 4,067,691 | 1/1978 | McGrady et al. . |
| 4,164,538 | 8/1979 | Young et al. . |
| 4,203,943 | 5/1980 | Gillis et al. . |
| 4,261,950 | 4/1981 | Bainbridge et al. . |
| 4,309,381 | 1/1982 | Chamberlain et al. . |
| 4,447,394 | 5/1984 | Krouthen . |
| 4,447,399 | 5/1984 | Runnells et al. . |
| 4,592,896 | 6/1986 | Runnells et al. . |
| 4,908,188 | 3/1990 | Jefferis, III et al. ................. 422/28 |
| 5,008,079 | 4/1991 | Wutzler et al. ....................... 422/28 |

FOREIGN PATENT DOCUMENTS 2921915 12/1980 Fed. Rep. of Germany .
2544615 10/1984 France .

Primary Examiner—Timothy M. McMahon
Attorney, Agent, or Firm—Trask, Britt & Rossa

[57] ABSTRACT

A chemical sterilizer system for sterilizing items by vaporizing a liquid chemical sterilant in a sterilizing chamber. Pre-evacuation of the sterilizer chamber enhances the sterilizing activity. Sterilant is injected into the sterilizer chamber from a prefilled shot chamber. Subsequent to the exposure period, spent sterilant is condensed and fresh air is pumped into the sterilizer chamber from a vacuum pump. An automated valving system uses a minimal number of three-way valves and one or more two-way valves to control the fluid flow functions in the sterilization cycle.

4 Claims, 22 Drawing Sheets

CHEMICAL STERILIZER SYSTEM

BACKGROUND OF THE INVENTION

1. Field

This invention relates to chemical vapor sterilizers. More particularly, this invention relates to methods and apparatus for the sterilization of items by vapors generated in a small sterilizer from injected liquid sterilants.

2. State of the Art

Chemical vapor sterilizers are well known. MDT Corporation of Torrance, Calif., markets such devices under the trademark "CHEMICLAVE ®," for example. Sterilizers of this type are characterized by a chamber into which a prescribed quantity of liquid sterilant chemical is introduced. The liquid is heated in the chamber, thereby creating chemical vapor sterilant. Modern systems include a reservoir for holding sufficient liquid sterilant chemical for several sterilization cycles. Sterilant is delivered in liquid form from the reservoir through a transport system to the sterilizing chamber.

Dental and medical clinics, schools, research laboratories and similar facilities often require sterilization of a few items. For small loads, a sterilizer sized to fit on a tabletop or countertop is especially advantageous.

In current chemical sterilizers, the sterilant is typically injected into the sterilizing chamber at atmospheric pressure. As a result, pockets of air or much-diluted sterilant may result in less than adequate sterilization throughout the chamber. Lengthening the exposure time is generally not a satisfactory solution.

In addition, since most facilities do not wish to invest in systems to vent the sterilizer out of doors, gases and vapors containing residual chemical sterilant components may be discharged directly into the interior of a room. The possibility exists for unacceptable levels of chemical irritants, e.g. formaldehyde, to accumulate in the room over a prolonged period.

The control systems, including the valving system, of current chemical sterilizers may also provide opportunities for undetected operator errors.

The need exists for a small chemical sterilizer which consistently provides the desired sterilization within a short turnaround time, is simple to operate, and prevents or minimizes the escape of sterilant components into the atmosphere.

SUMMARY OF THE INVENTION

The chemical sterilizer of this invention has a sealable heated sterilizer chamber supported by one or more subsystems:

(a) A sterilant injection subsystem stores the sterilant, measures a predetermined volume and injects it into the sterilizer chamber.

(b) An evacuation subsystem is engaged to the sterilizer chamber to evacuate the chamber to reduce dilution of the vaporized sterilant by air, and alternatively to pump fresh air into the sterilizer chamber to purge the spent sterilant therefrom.

(c) A purge system encompasses the evacuation means of the evacuation subsystem, but also includes means to cool and condense the spent sterilant. A waste reservoir collects the condensed sterilants, gases and vapors from the sterilizer chamber and acts as a liquid-gas separator. The gases and vapors are filtered to remove residual sterilant components, and the condensate is disposed of.

(d) A control subsystem includes appropriate valving (typically four three-way solenoid valves and at least one two-way valve); interconnecting conduits, and an electronic controller with sensor means for determining temperature, pressure, door position, valve positions and the like. The evacuation means, heater and valve positions are controlled to provide an automated chemical sterilizer with highly effective sterilization, shortened cycle time, and effective containment/treatment of chemical sterilant components. The automated system results in a sterilizer with simplified operation and reduced possibilities for operational errors.

Various embodiments of the invention may be configured to provide a chemical sterilizer in which loss of sterilant activity due to dilution with air or sterilizer gases is greatly reduced. The sterilant dose may be automatically and accurately premeasured during the prior sterilization cycle. The number of required control valves is minimized.

Several features of the invention combine to reduce the discharge of chemical sterilant components to a low level, to enhance safety and meet governmental standards.

Other benefits which may be realized by incorporating the subsystems of this invention in various embodiments include the preservation of sterilant activity which would otherwise be lost by virtue of dilution by the contained atmosphere of the sterilization chamber; the reduction of variations in sterilization conditions at different locations within the sterilization chamber; a reduction in the number of control valves required for a chemical sterilization system; the capability to automatically meter a sterilant dose for a subsequent sterilization cycle during the course of a cycle in progress, thereby reducing the time required for a series of cycles; and the overall enhancement of the sterilization procedure from the standpoints of safety and reliability.

The sterilizer of this invention is particularly in a countertop version for sterilizing relatively small loads. The sterilizer has a short turnaround time, minimal variability in sterilizing conditions, and enhanced safety. Its operation is simple and largely automated.

BRIEF DESCRIPTION OF THE DRAWINGS

In the drawings, which illustrate what is presently regarded as the best mode for carrying out the invention.

DETAILED DESCRIPTION OF THE ILLUSTRATED EMBODIMENT

Figure 1:
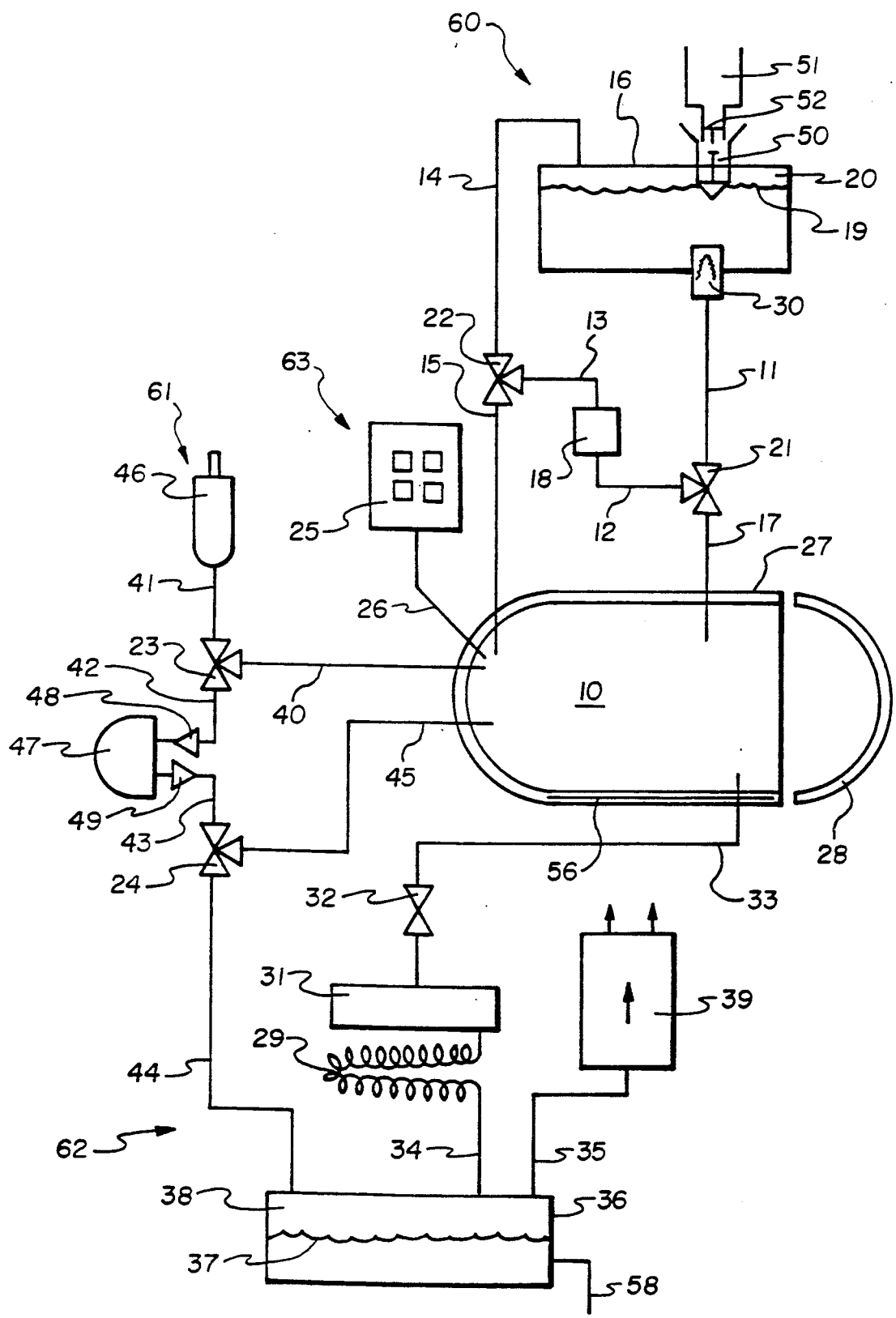
FIG. 1 is a schematic view of a chemical vapor sterilizer of this invention.

As illustrated in FIG. 1, the components of the sterilizer of this invention include sterilizer chamber 10 which has insulated walls 27 and a sealable door 28. Preferably, the door 28 is insulated to achieve approximately the same thermal resistance as the walls 27 to avoid uneven heating and condensation on the inside of door 28.

The sterilizer also includes a sterilant injection subsystem 60, an evacuation subsystem 61, a purge subsystem 62 and a control subsystem 63. The sterilizer components including the subsystems are enclosed in a tabletop or countertop cabinet for convenient use in medical, dental, scientific and other facilities. The only utility required is electrical power.

Sterilant injection subsystem 60 includes sterilant reservoir 16 for holding liquid sterilant chemical for delivery to the sterilizer chamber 10 via shot chamber 18. The reservoir has a filling port 50 by which sterilant may be transferred from container 51 through dispenser 52. The preferred filling port 50 and dispenser 52 have the construction and method of use as described and claimed in commonly assigned, copending U.S. Pat. application Ser. No. 468,770 filed Jan. 23, 1990, of John C. Schmoegner et al. titled RESERVOIR DISPENSING SYSTEM FOR CHEMICAL STERILIZER (identified as case 1568 in the internal files of applicant.) The apparatus of that application enables the filling of reservoir 16 to a liquid level 19 which provides vapor space 20 and prevents escape of vapors to the atmosphere. The entire disclosure of the aforesaid application Serial No. 468,770, is incorporated herein by reference.

Sterilant reservoir outlet conduit 11 leads to the third port of a first three-way solenoid valve 21. Valve 21 has a first port from which a first conduit 17 extends to sterilizer chamber 10.

An additional conduit 14 leads from vapor space 20 of sterilant reservoir 16 to a third port of a second three-way solenoid valve 22. A first conduit extends from a first port of valve 22 to sterilizer chamber 10.

A second conduit 12 connected to a second port of first three-way valve 21 extends to the lower portion, preferably the bottom, of shot chamber 18. Similarly, three-way valve 22 is connected to the top of shot chamber 18 by conduit 13. When valves 21 and 22 are activated to a first open position, permitting flow between the shot chamber 18 and reservoir 16, sterilant solution will flow by gravity through conduit 11, valve 21, conduit 12, shot chamber 18, conduit 13, valve 22, and into conduit 14 to equilibrate at the liquid level 19 of sterilant in reservoir 16. This "open loop" flow path ensures rapid and complete filling of shot chamber 18 and conduits 12 and 13.

The combined volume of the shot chamber 18 and conduits 12 and 13 provides the desired quantity of sterilant to be delivered to sterilizer chamber 10 in a single sterilizing cycle.

The shot chamber 18 is situated above the sterilizer chamber 10, and the sterilant reservoir 16 is situated above the shot chamber 18 to ensure rapid flow by gravity from reservoir 16 to shot chamber 18 and then to sterilizer chamber 10.

Preferably, a filter 30 is placed in conduit 11 to prevent any solids present in the reservoir contents from reaching and clogging or damaging the solenoid valves.

Following pre-evacuation of sterilizer chamber 10 by vacuum pump 47, valve 23 to the vacuum pump is closed and liquid sterilant is introduced into the sterilizer chamber 10 by simultaneously activating both valves 21 and 22 to close the flow paths from reservoir 16 and open them to flow between sterilizer chamber 10 and shot chamber 18. Liquid sterilant in conduits 12 and 13 and in shot chamber 18 flows rapidly and completely into chamber 10 by gravity, because of the open loop low pressure equalization. Valves 21 and 22 are then deactivated and shot chamber 18 and conduits 12 and 13 are refilled in preparation for the next sterilization cycle.

The evacuation subsystem 61 includes a small vacuum pump 47 having its inlet 48 connected by conduit 42 to third three-way solenoid valve 23 and its outlet 49 connected by conduit 43 to fourth three-way valve 24. The other two ports of three-way valve 23 lead via conduit 40 to sterilizer chamber 10, and via conduit 41 to the atmosphere. Filter 46 removes particulate matter from air drawn into conduit 41 during purging of the sterilizing chamber.

The other two ports of three-way valve 24 are connected via conduit 45 to sterilizer chamber 10, and via conduit 44 to waste reservoir 36. The latter is part of purge subsystem 62.

The Thomas Series 107 vacuum pump manufactured by Thomas Industries, Inc. of Sheboygan, Wis. is particularly well adapted to this invention. Vacuum pump model number 107 CA 16 is capable of quickly attaining and maintaining a vacuum of at least $-7$ (minus 7) pounds per square inch gauge (PSIG), which at sea level is essentially equivalent to an absolute pressure of about 400 mm Hg. Pre-evacuating the sterilizer chamber to this pressure will remove nearly one-half of the air, resulting in a shorter "fill time" for injecting the liquid sterilant into the sterilizer chamber.

For example, the fill time may be reduced from 20 minutes to about 7 minutes by use of pre-evacuation. Furthermore, the reduced air mass in the chamber permits a greater quantity of sterilant to be used. The reduced dilution by air enhances the sterilizing activity of the vaporized sterilant.

In addition to waste reservoir 36, the purge subsystem also includes conduit 33 leading from sterilized chamber 10 to solenoid valve 32 and thence to a massive aluminum cold bar 31, through cooling coil 29, and through conduit 34 to waste reservoir 36. Sterilant vapors passing to the aluminum bar 31 and cooling coil 29 are quickly cooled to approximately room temperature, condensed and delivered to the waste reservoir 36. Air and other gasses pass via conduit 35 to filter 39 where the small quantities of sterilant components such as formaldehyde and other contaminants are removed. The filtered gas is discharged to the atmosphere. A liquid level 37 is maintained in waste reservoir 36 to provide vapor space 38. Discharge through conduit 58 of condensed sterilant is controlled by conventional means, not shown, to maintain the proper liquid level 37.

Cold bar 31 is a massive aluminum bar bored for fluid flow. It acts as a passive heat sink for quickly absorbing a large part of the spent sterilant's enthalpy. For a small tabletop sterilizer, an aluminum bar of 15 to 36 cubic inches will provide the required heat capacity.

A preferred exhaust filter system for removing residual chemical components from the waste vapors is described and claimed in a commonly assigned, copending U.S. Pat. application Ser. No. 463,442, filed Jan. 11, 1990. titled EXHAUST FILTER SYSTEM FOR STERILIZERS of John C. Schmoegner et al. The entire disclosure of now U.S. Pat. No. 5,022,898, is incorporated herein by reference. This filter system includes a liquid trap filter for capturing condensed fluids. and a canister filled with a reactive or inert chemical composition which detoxifies or captures spent sterilant components of the exhaust gases.

In practice, a pressure relief valve is installed on chamber 10 or an attached conduit such as conduit 40, as required by law and good engineering practice.

In addition, a check valve may be included in conduit 45 to ensure that sterilant vapors will not pass from chamber 10 to the vacuum pump 47. Such vapors may adversely affect the materials of construction of the pump.

A control subsystem 63 includes electronic control unit 25, pressure/temperature measurement means 26, and other measurement means, not shown. It is understood that electrical and electronic control wires, not shown, connect unit 25 to the various solenoid valves 21, 22, 23, 24 and 32, vacuum pump 47, temperature and pressure measurement devices and the like. Control unit 25 controls the sequence of operations necessary to perform the desired sterilization.

Figure 2:
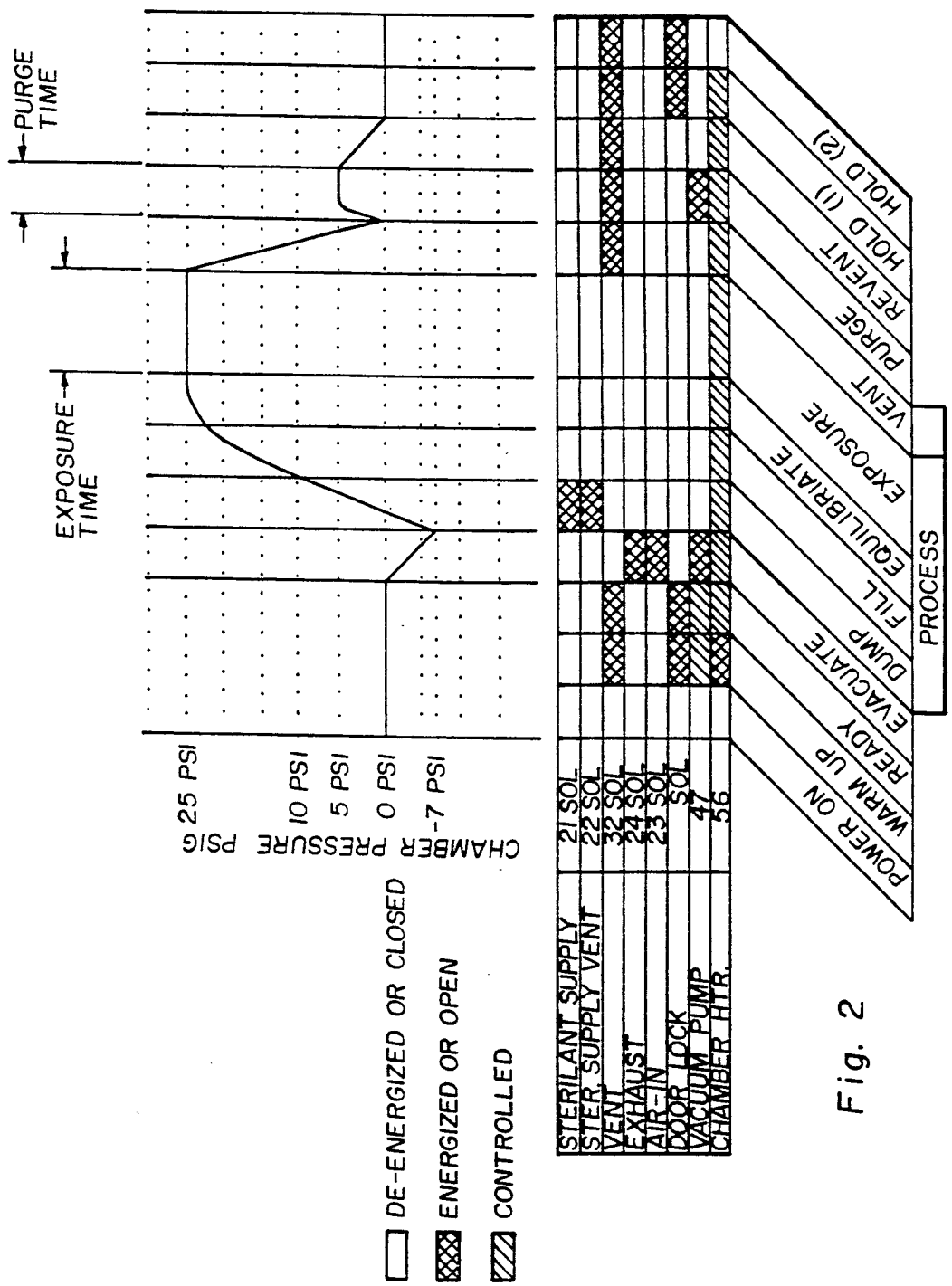
FIG. 2 is a graphical representation of a typical pressure curve characteristic of a typical operation of the chemical vapor sterilizer of FIG. 1.

FIG. 2 graphically depicts the typical sterilizer chamber gauge pressure at each step in the sterilization process, following loading of the chamber. The figure also shows the position of the various solenoid valves 21, 22, 23, 24 and 32, as well as the condition of the vacuum pump means 47, sterilizer chamber door lock (typically a solenoid type lock), and sterilizer-chamber heater 56. The latter two components are not shown in FIG. 1, but are well-known in the field of sterilizers. Typically, one or more electrical band heaters surround the cylindrical portion of the sterilizer chamber, lying between the metal wall of the chamber and the external insulation.

As already indicated, each three-way solenoid valve has three ports for flow. It is understood that the possible valve positions include:

(a) a "de-energized" position in which fluid flow may take place between the second port and the third port, and (b) an "energized" or "open" position in which flow may take place between the first port and the second port.

While the three-way valves may also provide (c) a "totally closed" position to restrict flow in all ports, or (d) a "totally open" position in which flow is permitted in all ports, or (e) a position in which fluid flow may take place between the first port and the third port, none of these valve positions is required or used in the presently preferred embodiments of this invention. Use of valves having more than two flow positions may be detrimental by introducing the possibility for unsatisfactory sterilization or other hazard resulting from erroneous valve positioning.

The stages of a typical sterilization cycle proceeding from a "cold start" are shown in FIG. 2. The cycle is begun with all solenoid valves in the deenergized position, the door 28 lock de-energized, vacuum pump 47 off, and heater 56 off. Valves 21 and 22 are in a de-energized condition, so shot chamber 18 is already filled with sterilant. Upon turning the power on, solenoid valve 32 is opened, chamber heater 56 is energized to begin heating, and the door lock is energized to an unlocked position.

Vacuum pump 47 is also started and pumps atmospheric air through filter 46, conduits 41, 42. 43, and 45 into chamber 10. Air may leave chamber 10 through the door and/or through valve 32, which is open. Control panel indicators such as lights indicate whether there is sufficient sterilant in reservoir 16, whether liquid level 19 is too high, and whether canister filter 39 is in place.

Materials to be sterilized, typically in a tray, are then placed in chamber 10, and door 28 is closed and locked. During this period, the sterilizer chamber 10 is unpressurized, i.e. at 0 PSIG, and it is being heated to a desired vaporization temperature. The temperature selected will depend upon the particular sterilant in use, but typically is about 132° C. for common chemical sterilants largely composed of alcohols with smaller concentrations of ketones and formaldehyde.

Following closure of door 28, solenoid valves 23 and 24 are "exercised," i.e., cycled on and off several times, typically five times, to dislodge any particles such as formaldehyde deposits, in the valves and to assure operability of seals.

Solenoid valves 23 and 24 are then simultaneously activated in an evacuate step to open flow of gases, e.g. air from sterilizer chamber 10 through conduit 40, valve 23, conduit 42, vacuum pump 47, conduit 43, valve 24 and conduit 44 to waste reservoir 36. The gases are discharged from reservoir 36 through filter 39.

Two-way solenoid valve 32 is also deactivated to a closed position, and chamber 10 is evacuated to a pressure of about −5 (minus 5) to −8 (minus 8) PSIG. The chamber pressure at the end of the evacuation step is shown in FIG. 2 as −7 (minus 7) PSIG.

The "dump" or "sterilant injection" step is then begun by simultaneously activating solenoid valves 21 and 22, as previously described, to permit sterilant in shot chamber 18 and conduits 12 and 13 to flow into sterilizer chamber 10. Metal instruments in the chamber quickly absorb heat to create an additional small vacuum effect, which speeds the already rapid filling process.

Vaporization of the sterilant increases the total pressure in chamber 10. At a preset chamber pressure of 3 to 12 PSIG, typically 4 PSIG, solenoid valves 21 and 22 are deactivated to open the shot chamber 18 and associated conduits to sterilant flow from reservoir 16.

At the moment valves 21, 22 are deactivated, the higher pressure in shot chamber 18 creates backflow through filter 30 for an instant, and this backflow clears particulate matter from filter 30. The backflow vapors are quickly condensed and the pressure equalizes. As it does so, liquid sterilant refills the shot chamber and associated conduits in preparation for the next sterilization cycle.

The pressure in chamber 10 continues to rise to the vapor pressure of sterilant and air, at the extant temperature, typically 20–25 PSIG at a controlled temperature of about 132° C. The pressure is dependent upon the quantities of sterilant and residual air in the chamber, the sterilant composition, the chamber volume, and the temperature. As the temperature, and associated vapor pressure, equilibrate at the desired sterilization value, the exposure time of the materials undergoing sterilization is measured and controlled. Typically, the exposure times may be in the range of 7 to 20 minutes, depending upon the load size. The shorter exposure time is useful for sterilizing a small number of unwrapped medical or dental instruments.

Upon reaching the desired exposure time, a "vent" step is initiated. Two-way solenoid valve 32 is activated to an open position. Pressurized vapors flow from chamber 10 through bar 31 and cooling coil 29, and are cooled to nearly room temperature, i.e. 25–30° C. and condensed. The condensate is collected in waste reservoir 36 for subsequent disposal. Gases and vapors pass through filter 39 to remove traces of sterilant components. The chamber pressure falls to 0 PSIG as the spent sterilant is discharged.

When the chamber 10 attains a reduced pressure, preferably approximately atmospheric, solenoid valve 24 is activated so that the vacuum pump 47, operating since the "warm up" step, begins to pump atmospheric air from filter 46 through conduit 41, valve 23, conduit 42, pump 47, conduit 43, valve 24 and conduit 45 to the sterilizing chamber 10. The entering airstream is lower in temperature than the chamber or its contents. As it enters at the back of the chamber, it tends to drop, being heavier than the hot vapors. The air is heated by contact with the chamber walls and by mixing with the hot vapors and subsequently rises and mixes further with and dilutes the hot vapors. In a small chemical sterilizer, a seven minute continuous purge is generally adequate to reduce the chemical constituents of the chamber gases to below OSHA requirements. Without this purge, a much longer time is required to meet this standard.

Following the timed purge, valve 24 and pump 47 are deactivated to cut off the purge air and permit the chamber to equilibrate by reventing at atmospheric temperature.

In a subsequent first "hold" condition, the door lock is activated to open the door and permit the removal of sterilized items. This "hold" condition permits initiation of another sterilization cycle with a shortened "warm up" time.

In a second, optional "hold" condition, the heater 56 is also deactivated to cool the chamber.

If desired, the entire sterilizer can be deactivated to return it to the original "off" condition.

The control system may be set to automatically start and shut down the sterilizer at any desired time, so that it is energized only during working hours, for instance.

FIGS. 3 through 14 show the various software routines useful in the control subsystem of the sterilizer.

Figure 3:
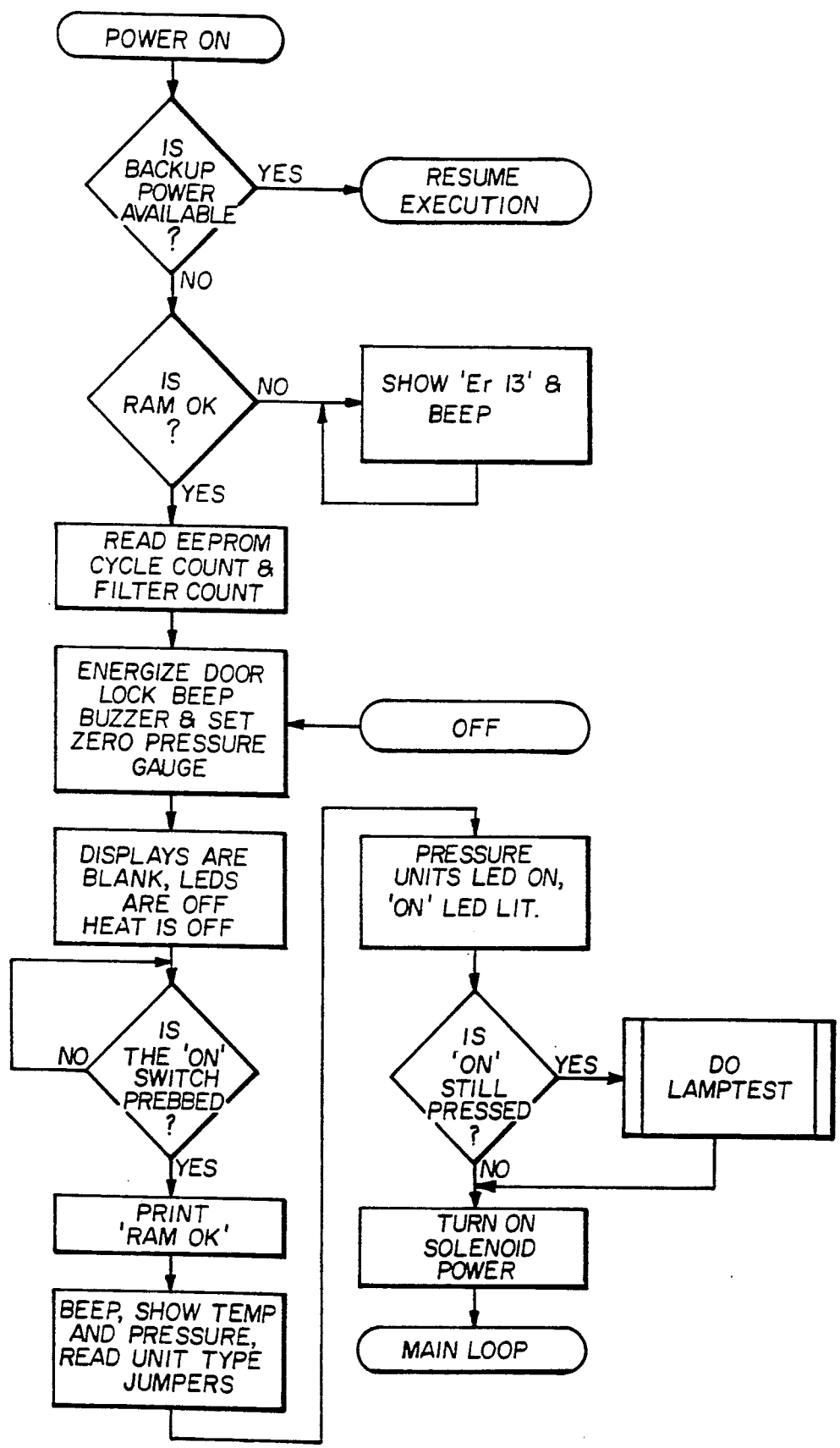
FIG. 3 is a block diagram of the power up software routine of an electronic control subsystem which may be used with a chemical sterilizer of this invention.

The "powerup" routine of FIG. 3 includes a cycle counter and a counter for the number of cycles which filter 39 has undergone. The system may be set to disable the sterilizer when a preset number of cycles following filter regeneration is reached. This routine also energizes the chamber door lock and sets the pressure gauge.

Figure 4:
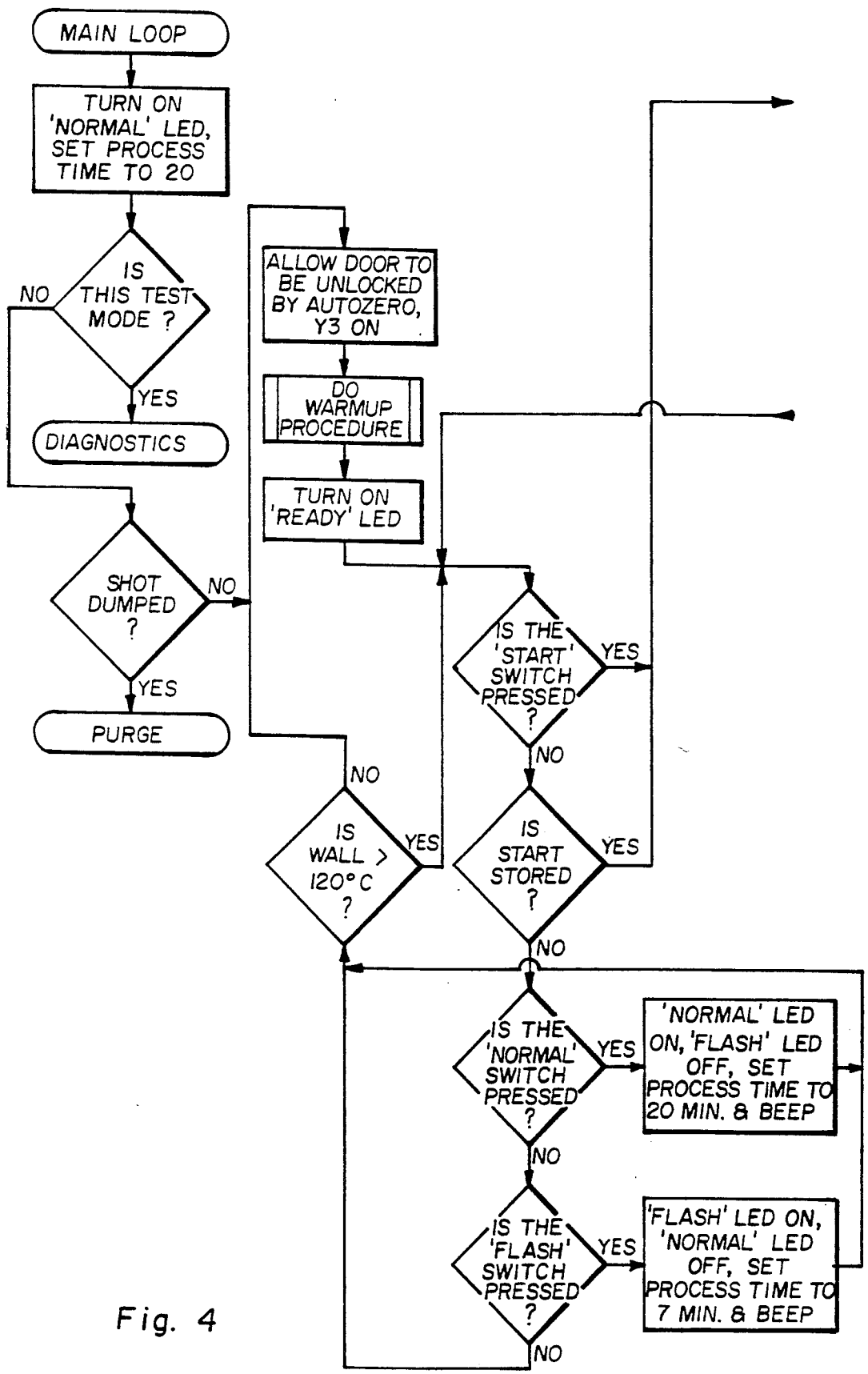
FIG. 4 is a block diagram of the main loop software routine of an electronic control subsystem useful with a chemical sterilizer of this invention.
Figure 4A:
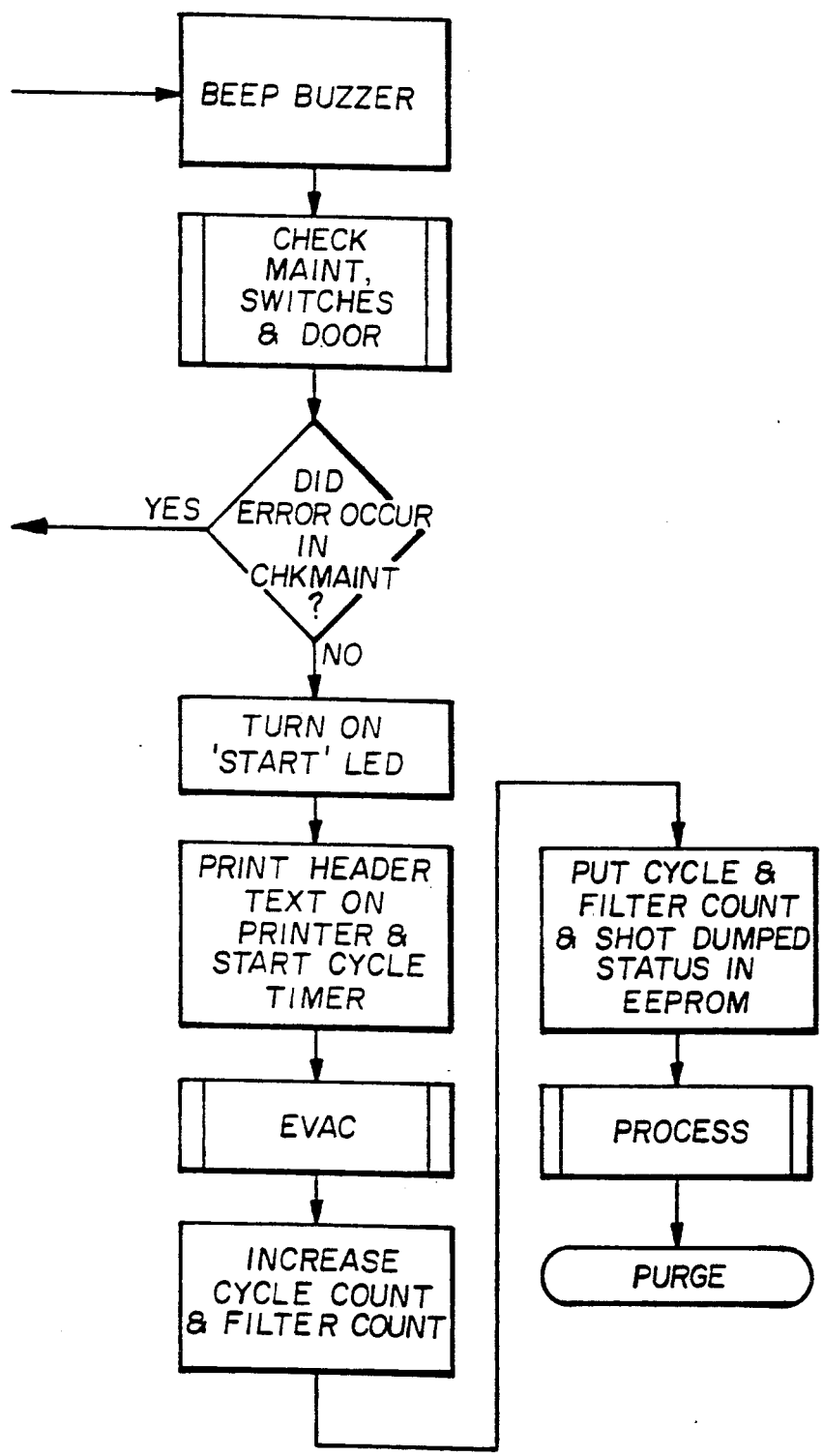
Figure 5:
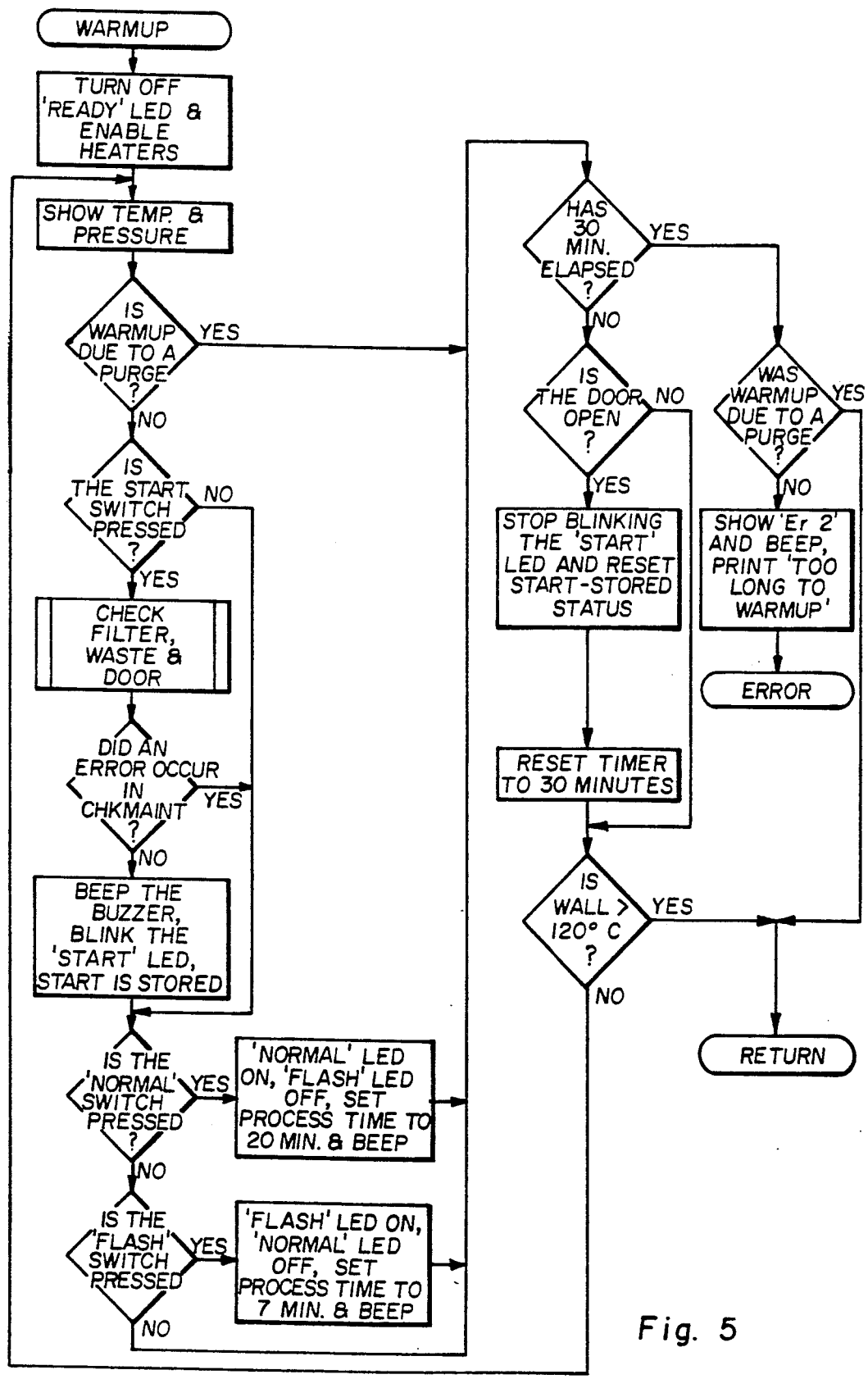
FIG. 5 is a block diagram of the warmup routine of an electronic control subsystem useful with a chemical sterilizer of this invention.
Figure 6:
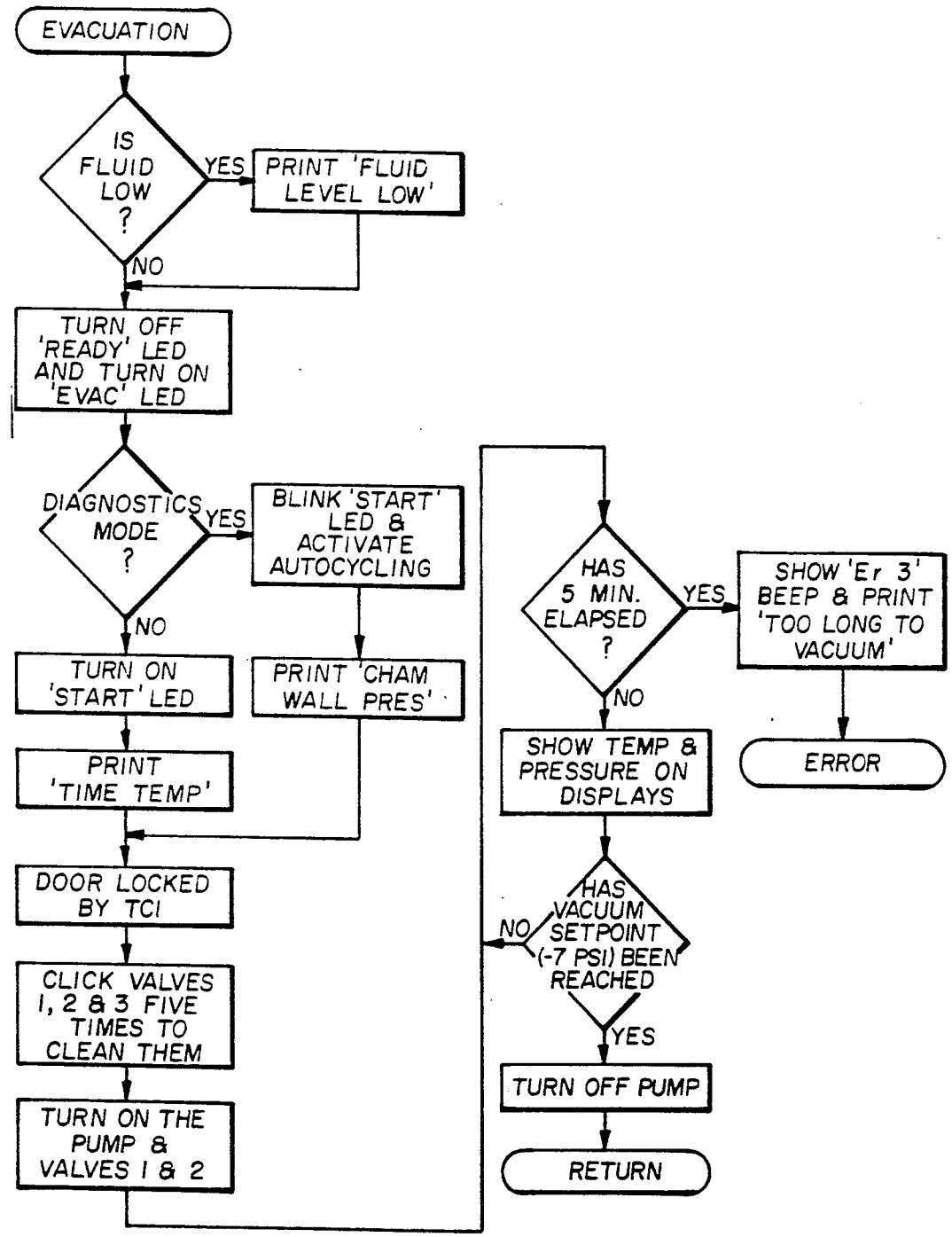
FIG. 6 is a block diagram of the evacuation routine of an electronic control subsystem useful with a chemical sterilizer of this invention.
Figure 7:
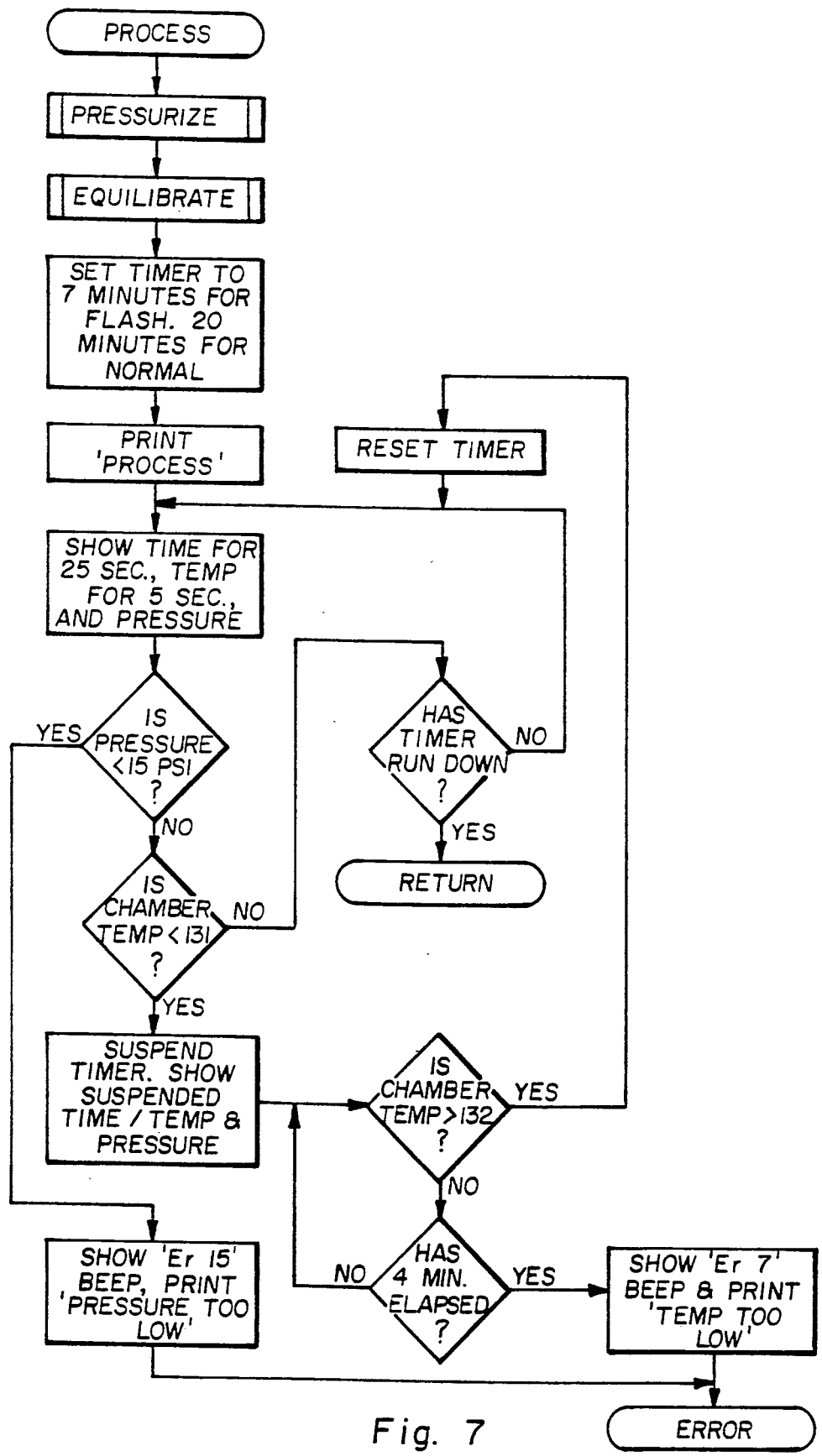
FIG. 7 is a block diagram of the process routine of an electronic control subsystem useful with a chemical sterilizer of this invention.
Figure 7A:
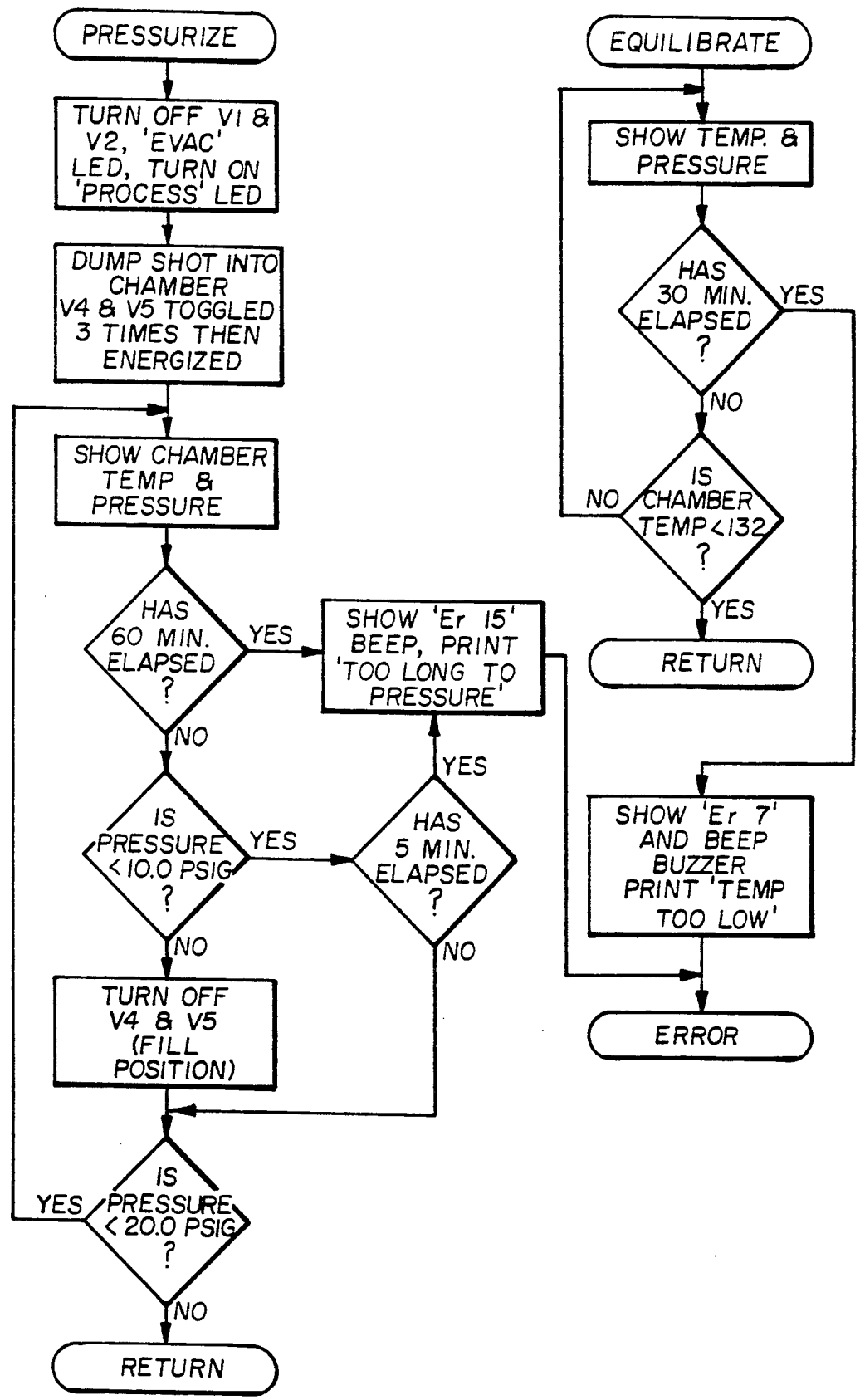
Figure 8:
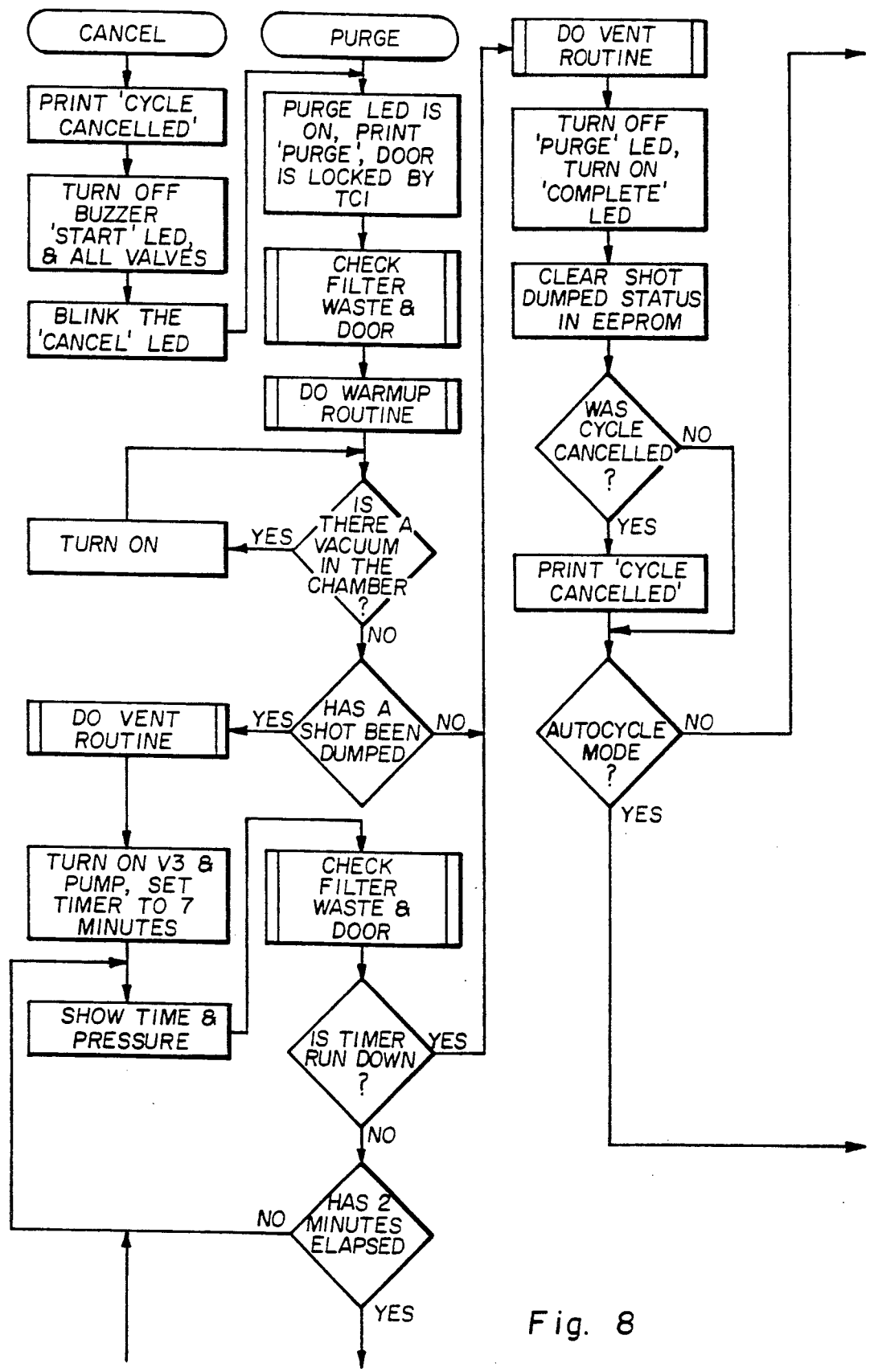
FIG. 8 is a block diagram of the purge routines of an electronic control subsystem useful with a chemical sterilizer of this invention.
Figure 8A:
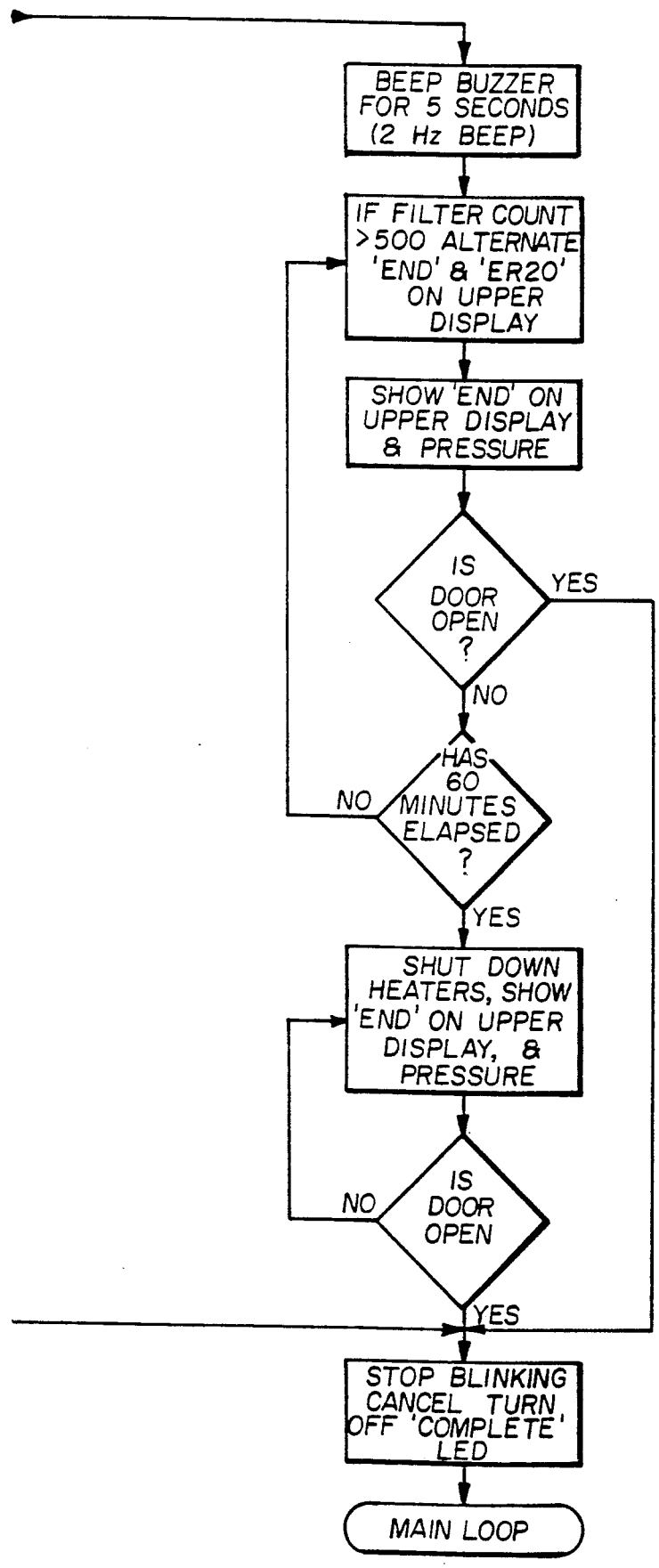
Figure 8B:
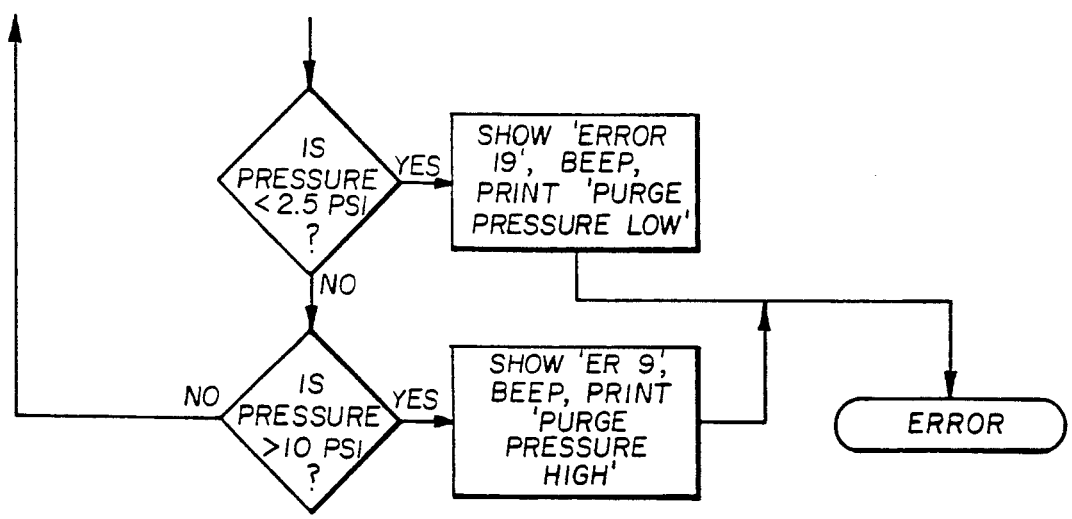
Figure 9:
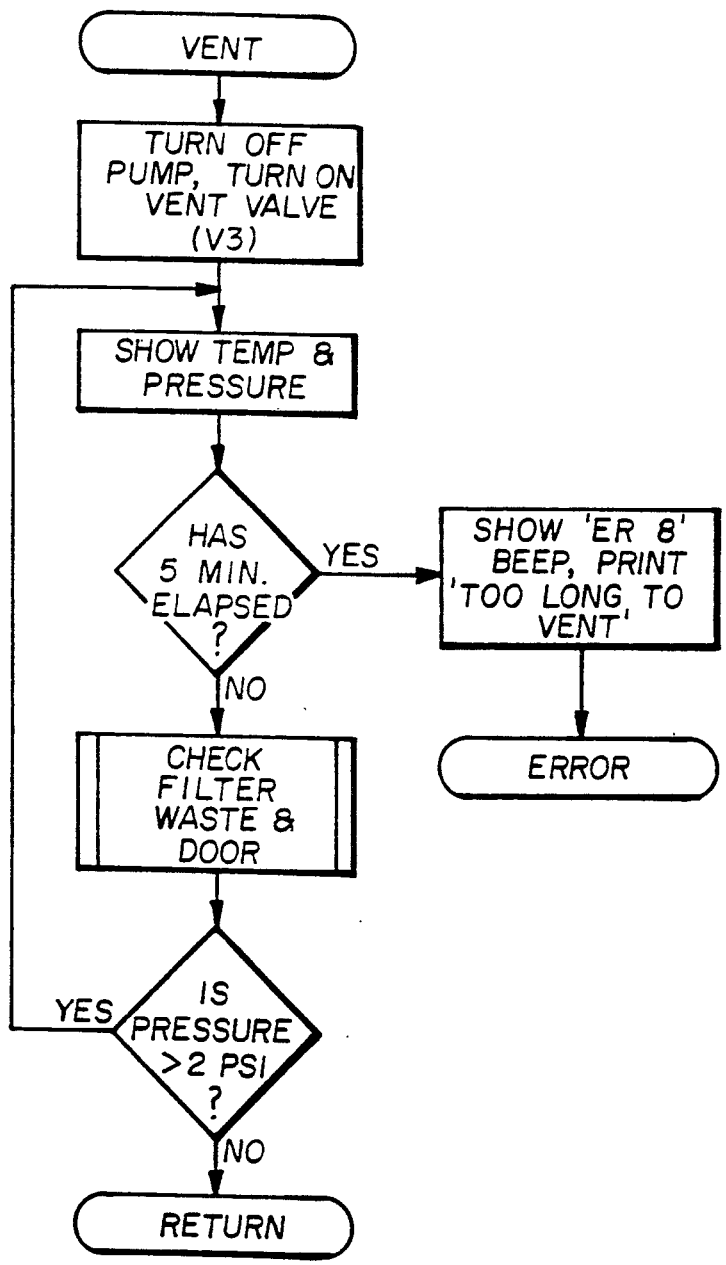
FIG. 9 is a block diagram of the vent routine of an electronic control subsystem useful with a chemical sterilizer of this invention.
Figure 10:
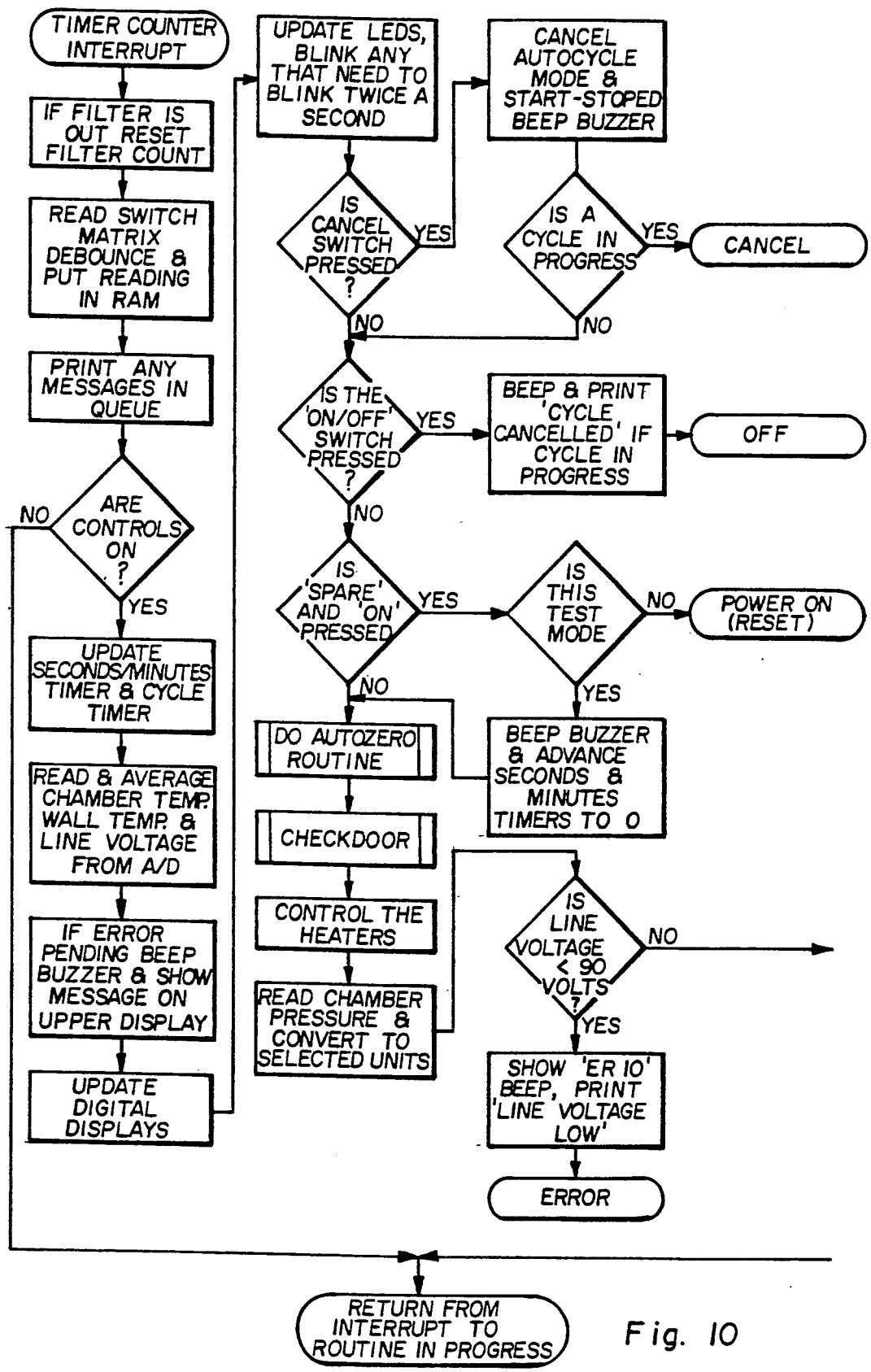
FIG. 10 is a block diagram of the timer-counter interrupt routine of an electronic control subsystem useful with a chemical sterilizer of this invention.
Figure 10A:
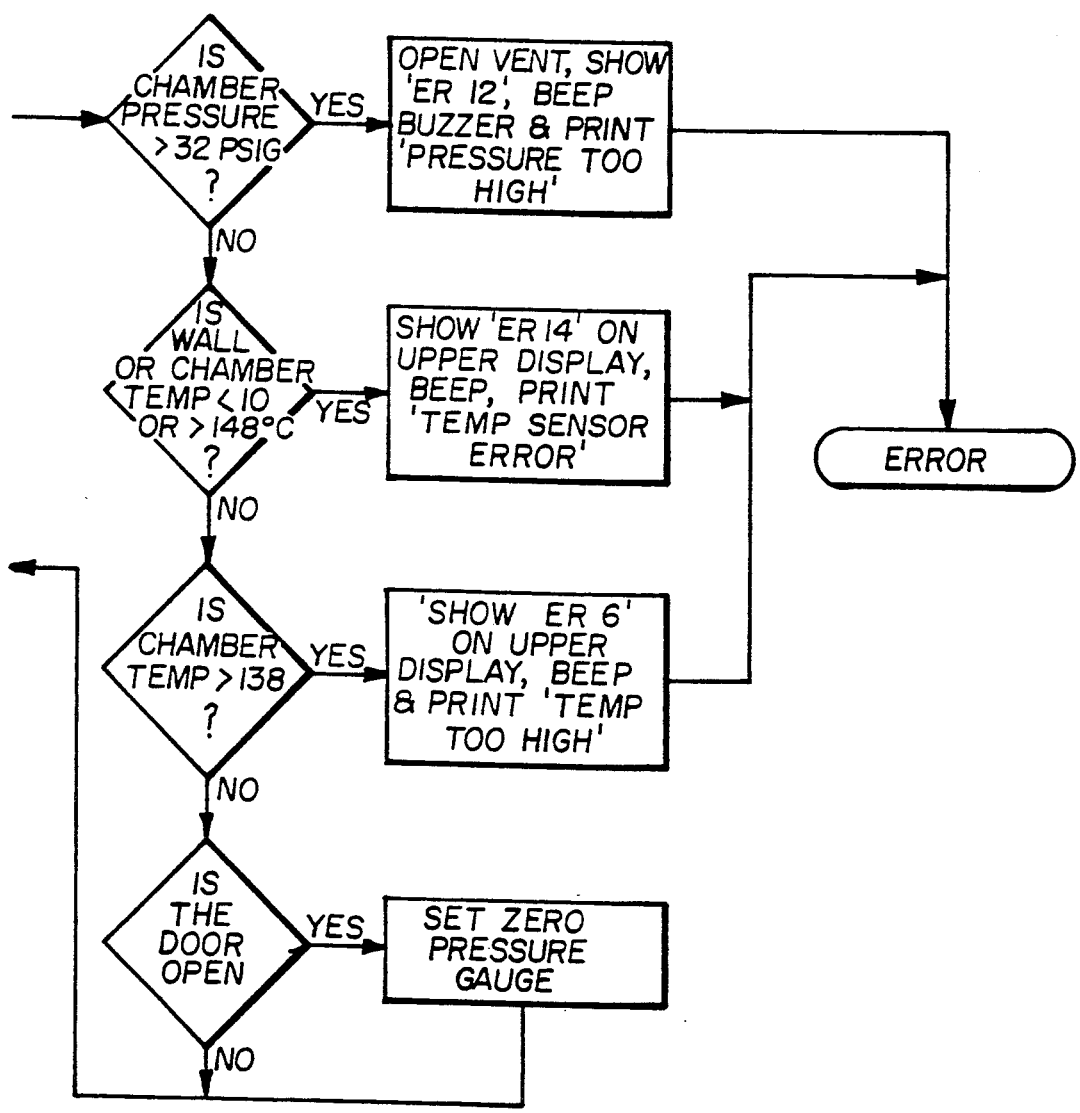
Figure 11:
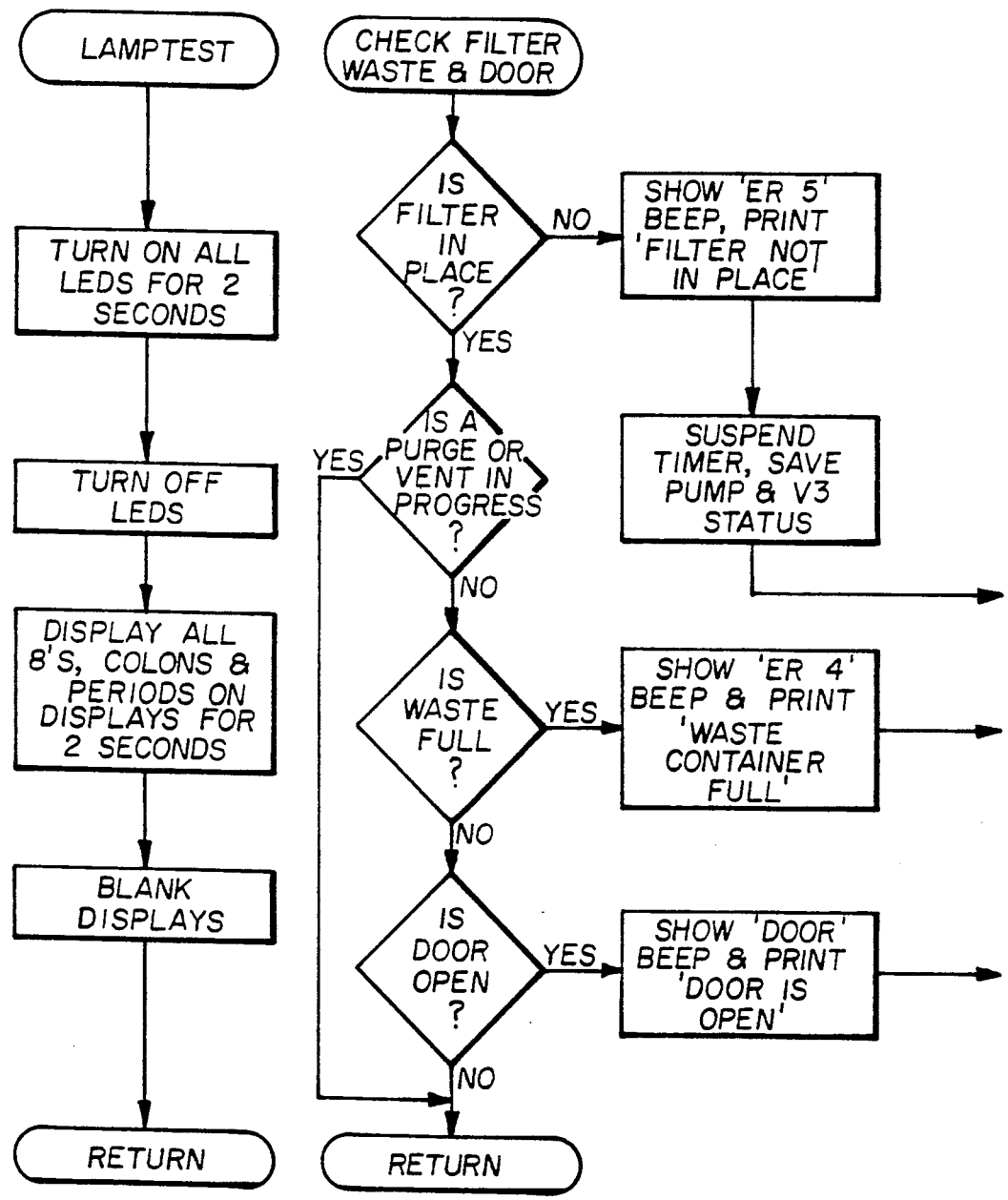
FIG. 11 is a block diagram of the lamptest routine and check maintenance indicators routine of an electronic control subsystem useful with a chemical sterilizer of this invention.
Figure 11A:
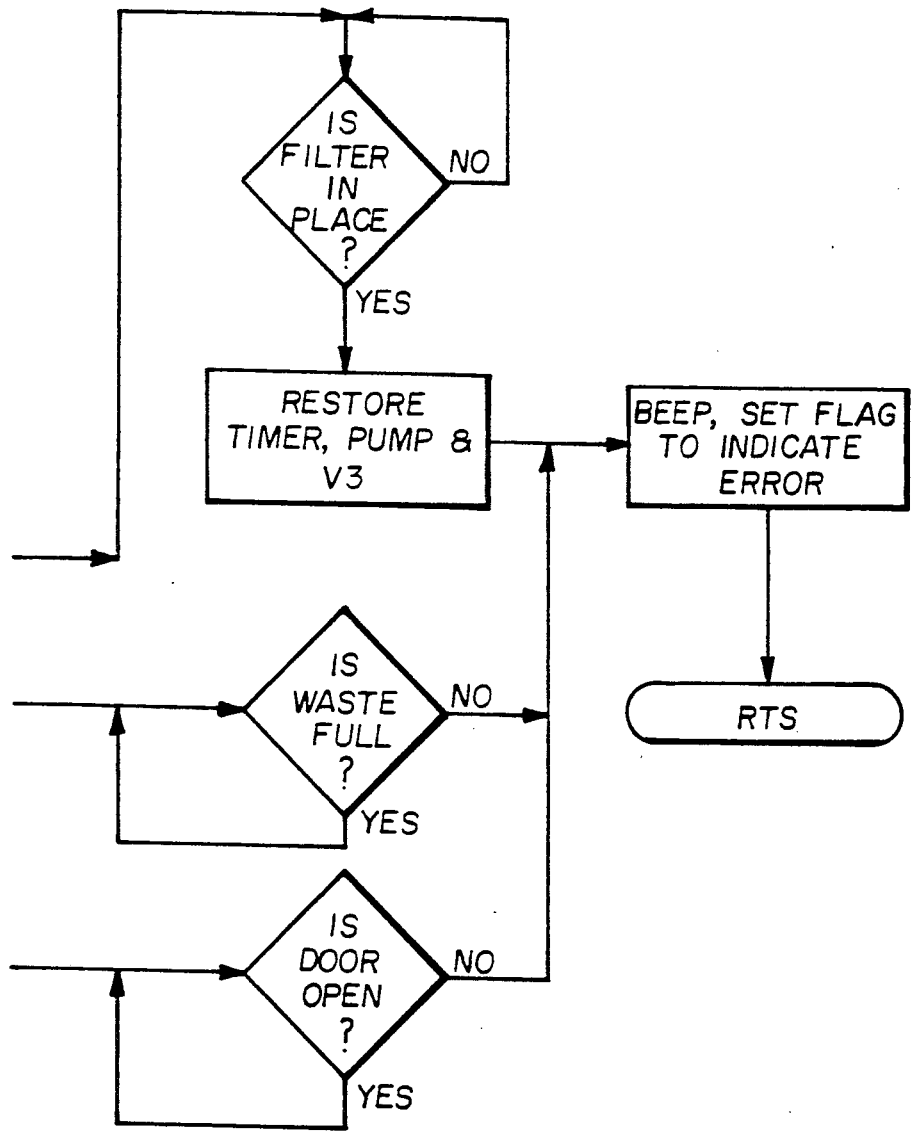
Figure 12:
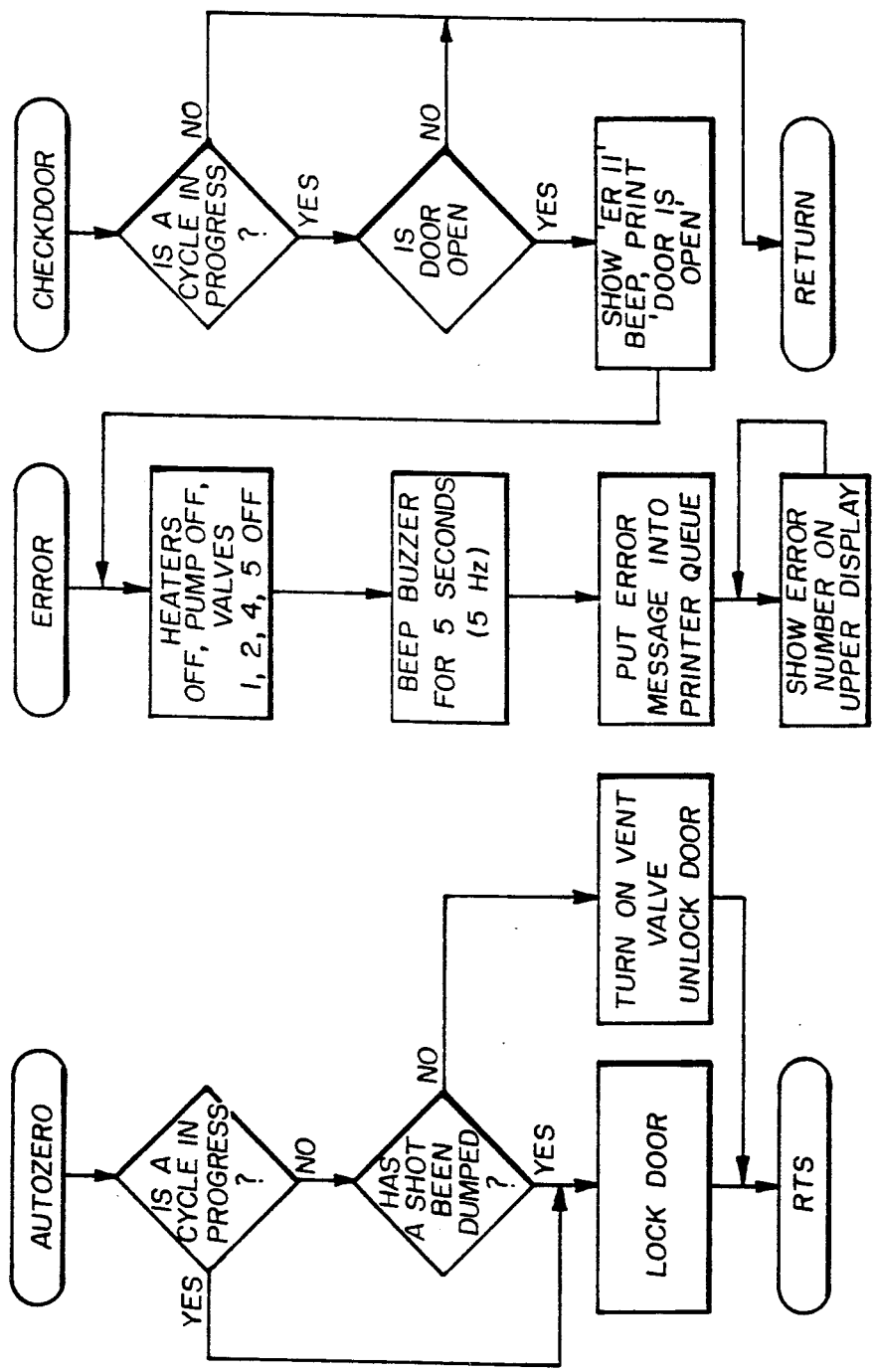
FIG. 12 is a block diagram of the autozero and error routines of an electronic control subsystem useful with a chemical sterilizer of this invention.
Figure 13:
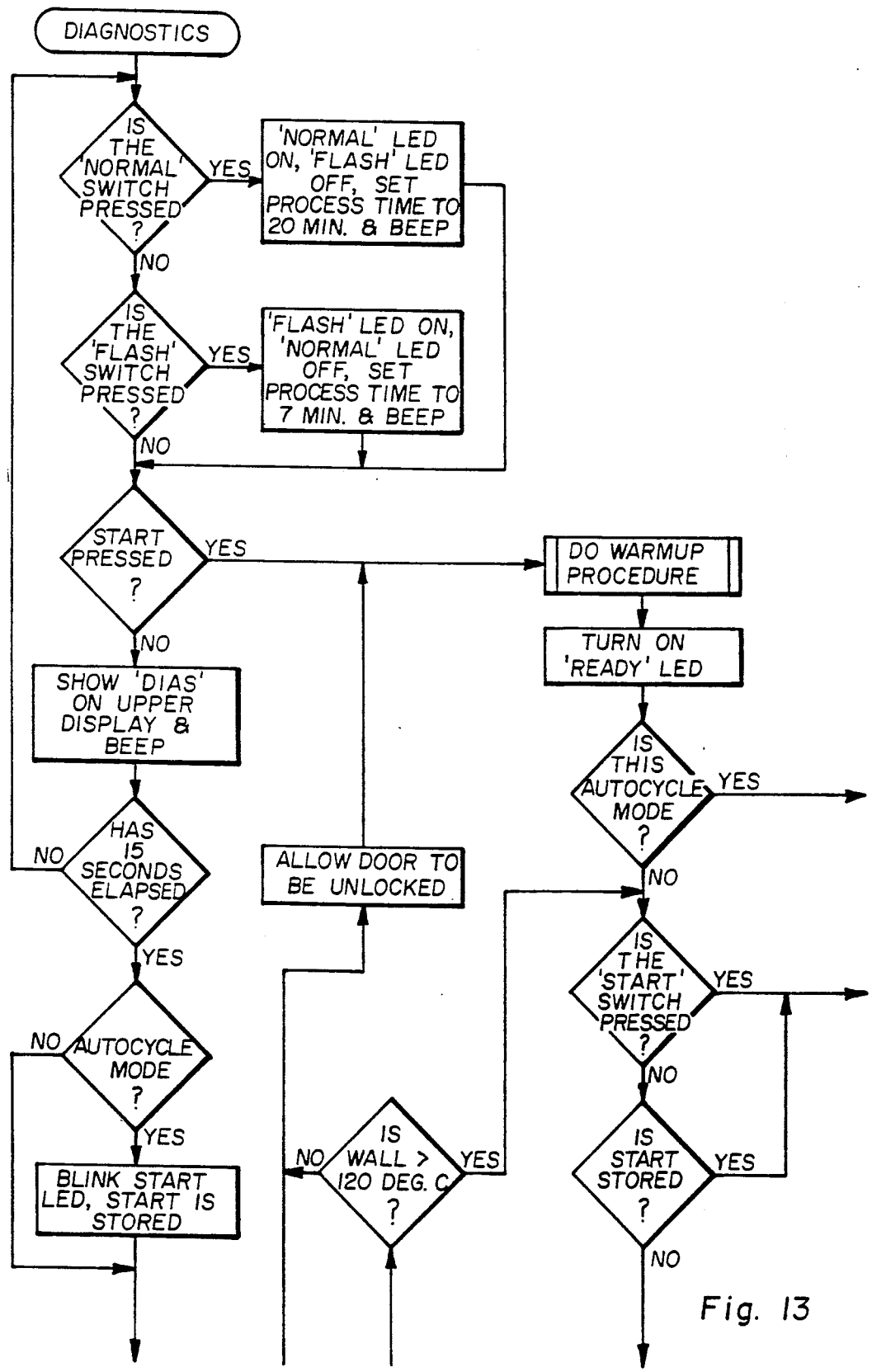
FIG. 13 is a block diagram of the diagnostics mainline routine of an electronic control subsystem useful with a chemical sterilizer of this invention.
Figure 13A:
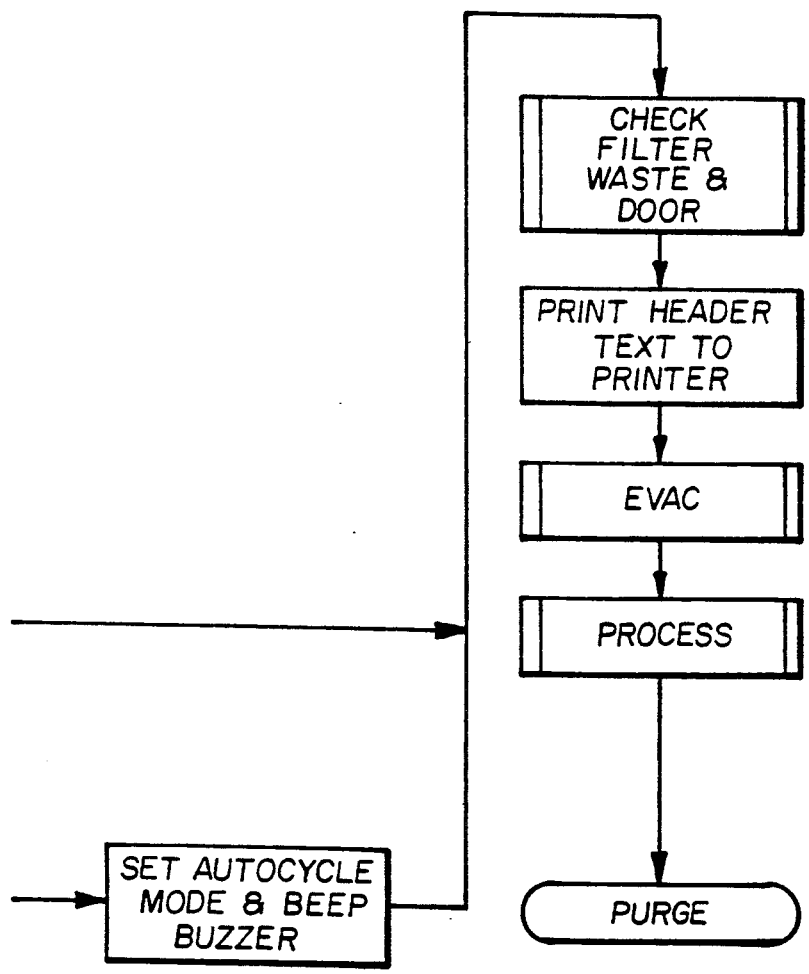
Figure 13B:
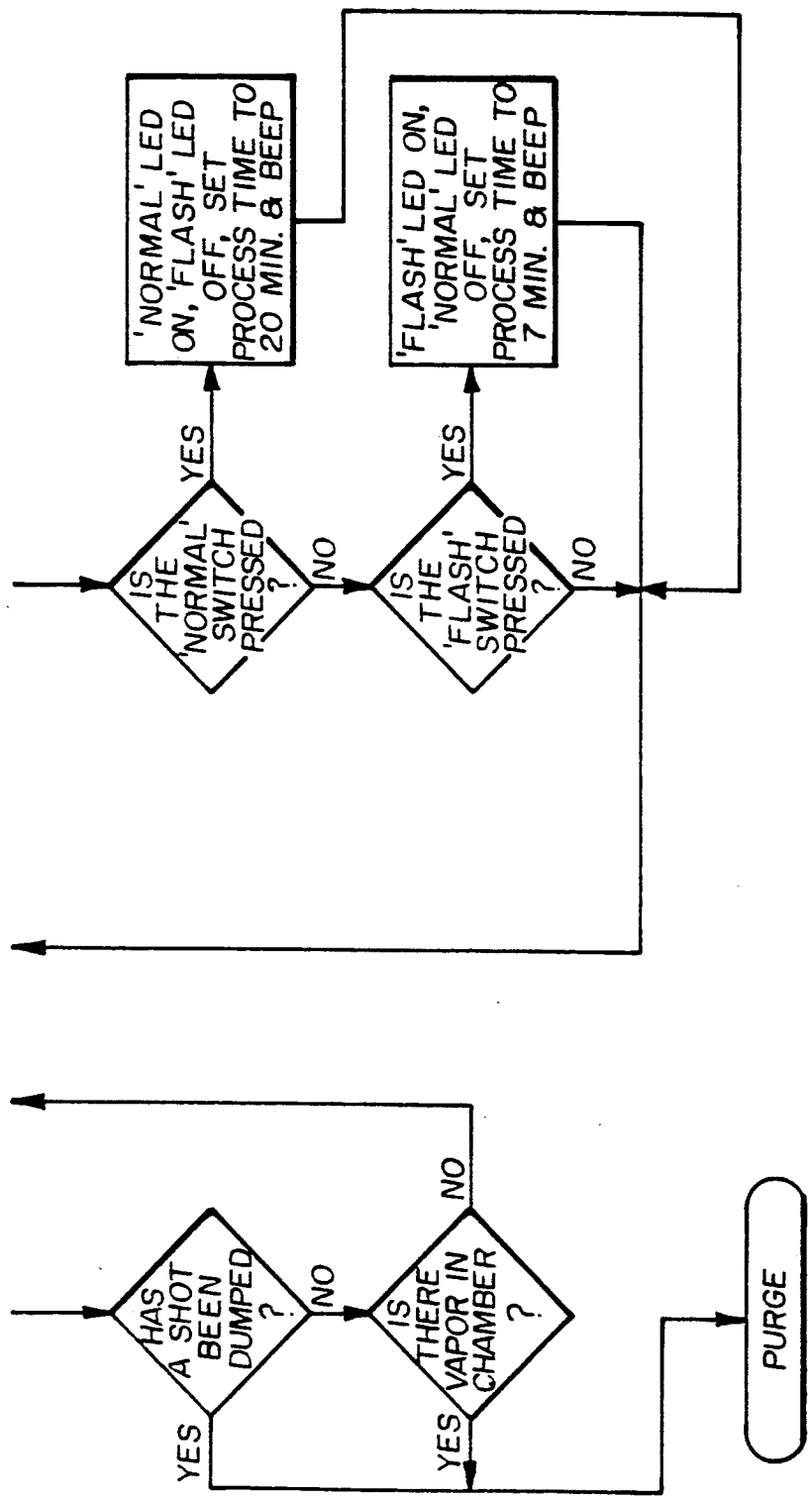
Figure 14:
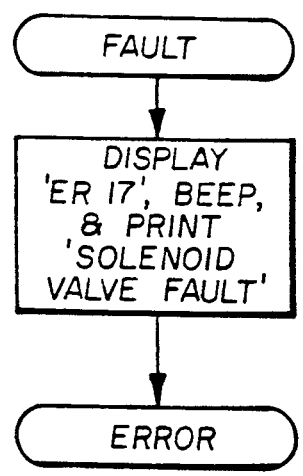
FIG. 14 is a block diagram of the solenoid valve fault routine of an electronic control subsystem useful with a chemical sterilizer of this invention.

The MAIN LOOP routine of FIG. 4 controls the process from warmup to purge and vent, using the warmup, evacuation process, purge, vent and timer-counter routines shown in FIGS. 5–10.

The various control routines for testing, maintenance checks, error disposition, diagnostics and valve fault are shown in FIGS. 11–14.

One important aspect of this invention is that of increasing the concentration of sterilant vapor in the sterilization chamber. With pre-evacuation, the sterilizing vapor will be composed of approximately equal parts of sterilant and air, by volume, based on the sterilization at 132° C. and 25 PSIG pressure. Pre-evacuation to −4 PSIG increases the sterilant vapor concentration to about 64 percent, pre-evacuation to −7 PSIG increases the sterilant vapor concentration to about 75 percent, and pre-evacuation to −10 PSIG increases the sterilant concentration to about 85 percent.

This increased concentration effectively enhances the sterilization action, and reduces the possibility for "air pockets" remaining in the chamber, and producing inadequate exposure of the materials to be sterilized.

Evacuation to very low pressures, i.e., near a complete vacuum, is not generally practical without a very large capacity vacuum pump, because of the great increase in time required to obtain smaller increments in pressure. Furthermore, the additional increase in effectiveness becomes insignificant.

Incorporation of the vacuum pump into the system for evacuating the sterilizer chamber enables another procedural step to reduce sterilant component emissions and to simultaneously shorten the cycle time. Following the sterilization exposure period, discharge of the spent sterilant from the sterilization chamber is assisted by directing air from the vacuum pump outlet to chamber 10. The introduced air increases the pressure, increasing the flow to the condensing elements 31, 29. During this purging period, the continuous dilution of spent vapors quickly reduces their concentration to a sufficiently low level to meet current governmental, e.g. OSHA, standards.

Another feature of this sterilizer is the automatic cleaning of filter 30. This cleaning occurs once each cycle, following injection or dumping of liquid sterilant into the sterilizer chamber 10. As this occurs, the pressures in sterilizer chamber 10 and shot chamber 18 immediately equilibrate at a pressure somewhat greater than atmospheric. As a result, when three-way solenoid valves 21 and 22 are simultaneously shut to the sterilizer chamber 10 and opened to the sterilant reservoir 16, an instantaneous pulse of pressurized sterilant vapors and air will flow back through conduit 11 and filter 30, blowing any solids from the inlet, i.e. reservoir side of the filter. A similar pulse occurs in valve 22 and conduit 14, blowing liquid sterilant back into reservoir 16. This emptying of conduit 14 permits the subsequent rapid filling of the shot chamber 18. Otherwise, the liquid in conduit 14 and in reservoir 16 are at the same level, tending to trap vapor and gases in shot chamber 18, i.e., between the two liquid heads, and preventing or slowing its filling.

Use of three-way valves in the arrangement described herein minimizes the number of valves required and enables efficient interaction between the valves and other components of each subsystem.

Reference herein to details of the illustrated embodiments is not intended to limit the scope of the appended claims.

What is claimed:

1. A method of sterilizing materials with a liquid chemical sterilant vaporized in a sealable, heated sterilizer chamber, comprising:

placing materials to be sterilized in said sterilizer chamber and sealing said sterilizer chamber;

heating said sterilizer chamber to a sterilant evaporation temperature;

pre-evacuating a portion of the atmosphere from said sterilizer chamber with a vacuum pump and producing a reduced pressure in said sterilizer chamber;

disengaging said vacuum pump from said sterilizer chamber at a predetermined reduced pressure therein;

introducing a predetermined quantity of said liquid chemical sterilant by gravity from a pre-filled shot chamber into said sterilizer chamber for vaporization therein and for mixture with residual atmosphere therein;

heating said sterilizer chamber and contents to a controlled sterilization temperature for vaporizing said introduced chemical sterilant;

maintaining said sterilization temperature for a timed period;

discharging spent vaporized sterilant and air from said sterilizer chamber through cooling means to condense and cool said vaporized sterilant;

engaging said vacuum pump to pump atmospheric air into said sterilizer chamber to rapidly cool said chamber and dilute said vaporized sterilant; and passing said discharged, cooled and condensed spent sterilant to a condensate reservoir for separating said condensed sterilant from gases and vapors.

2. The method of claim 1, further comprising:

the step following the introduction of said sterilant into said sterilizer chamber of disengaging said shot chamber from said sterilizer chamber and prefilling said shot chamber for a subsequent sterilization cycle.

3. The method of claim 1 wherein said gases and vapors are withdrawn from said condensate reservoir and are passed through a filter.

4. The method of claim 1 wherein said sterilizer chamber is provided with a solenoid valve control system, sterilant inlet conduit means, exhaust conduit means, a liquid sterilant reservoir means with a vapor space, sterilant injection means including said shot chamber for supplying sterilant to said sterilizer chamber means, evacuation means with a suction port and a discharge port, spent sterilant condensing means, waste reservoir means with a vapor space and a drain, and electronic control means, said solenoid valve control system comprising:

first three-way valve means with a first port connected by a first conduit to said sterilizer chamber, a second port connected by a second conduit to the bottom of said shot chamber, and a third port connected by a third conduit to said sterilant reservoir means;

second three-way solenoid valve means with a first port connected by a first conduit to said sterilizer chamber, a second port connected by a second conduit to the top of said shot chamber, and a third port connected by a third conduit to said vapor space of said sterilant means;

third three-way solenoid valve means with a first port connected by a first conduit to said sterilizer chamber means, a second port connected by a second conduit to said suction port of said evacuation means, and a third port connected by a third conduit to the atmosphere;

fourth three-way solenoid valve means with a first port connected by a first conduit to said vapor space of said waste reservoir means, a second port connected by a second conduit to said discharge port of said evacuation means, and a third port connected by a third conduit to said sterilant chamber;

first two-way solenoid valve means with a first port connected by a first conduit to said sterilizer chamber means and a second port connected by a second conduit to said spent sterilant condensing means; and condensate conduit means connecting said condensing means to said waste reservoir means;

wherein said first and second three-way valves are operable between a first position for filling said shot chamber with said liquid sterilant and a second position for injecting said liquid sterilant into said sterilizer chamber; and wherein said third and fourth three-way valves are operable between a first position for evacuating said sterilizer chamber, a second position for blocking flow to or from said sterilizer chamber, and a third position for purging said sterilizer chamber with air pumped by said evacuation means;

said solenoid valve control system being operated to effect said method.

* * * * *